US008182735B2

(12) United States Patent  
Edvardsson

(10) Patent No.: US 8,182,735 B2
(45) Date of Patent: *May 22, 2012

(54) APPARATUS AND METHOD FOR FORMING AIR-LAID ABSORBENT CORES

(75) Inventor: Gunnar Edvardsson, Bohus Björkö (SE)

(73) Assignee: SCA Hygiene Products AB, Gothenburg (SE)

(*) Notice: Subject to any disclaimer, the term of this patent is extended or adjusted under 35 U.S.C. 154(b) by 234 days.

This patent is subject to a terminal disclaimer.

(21) Appl. No.: 12/373,729

(22) PCT Filed: Jul. 20, 2006

(86) PCT No.: PCT/SE2006/050266
§ 371 (c)(1),
(2), (4) Date: Jan. 14, 2009

(87) PCT Pub. No.: WO2008/010751

PCT Pub. Date: Jan. 24, 2008

(65) Prior Publication Data

US 2010/0001426 A1    Jan. 7, 2010

(51) Int. Cl.
*B27N 3/08*    (2006.01)

(52) U.S. Cl. ........ 264/517; 264/299; 264/310; 264/319; 425/436 R

(58) Field of Classification Search .......... None
See application file for complete search history.

(56) References Cited

U.S. PATENT DOCUMENTS

| 3,973,291 A | 8/1976 | Kolbach |
| 4,388,056 A | 6/1983 | Lee et al. |
| 4,598,441 A | 7/1986 | Stemmler |
| 5,030,314 A | 7/1991 | Lang |
| 5,064,484 A * | 11/1991 | Craig et al. ............ 156/62.6 |
| 5,575,874 A | 11/1996 | Griesbach, III et al. |

(Continued)

FOREIGN PATENT DOCUMENTS

DE    1 510 427 B    10/1970

(Continued)

OTHER PUBLICATIONS

U.S. Appl. No. 12/373,780, Edvardsson, "An Apparatus and Method for Forming Air-Laid Absorbent Cores", filed Jan. 14, 2009.

(Continued)

*Primary Examiner* — Monica A Huson
(74) *Attorney, Agent, or Firm* — Buchanan Ingersoll & Rooney PC

(57) ABSTRACT

An apparatus for forming air-laid absorbent cores, having a first and second mat-forming wheel, each of the mat-forming wheels having a series of moulds along its peripheral surface, air-laying means for supplying air-entrained fibrous material to the moulds, suction means maintaining the formed core elements in their moulds during a part of the path of the moulds on the respective mat-forming wheel and means for transferring a core element on the second mat-forming wheel onto a core element on the first mat-forming wheel while the latter core element still is maintained in its mould, at least the air-laying means associated with the second mat-forming wheel having means for supplying a mixture of air-entrained fibrous material and discrete particles. The two mat-forming wheels form a nip between each other that the second core element will abut the first core element before transfer.

22 Claims, 3 Drawing Sheets

U.S. PATENT DOCUMENTS

| | | | |
|---|---|---|---|
| 6,330,735 B1 | 12/2001 | Hahn et al. | |
| 6,647,088 B1 | 11/2003 | Schmidt et al. | |
| 6,652,798 B1 * | 11/2003 | Edvardsson | 264/510 |
| 6,811,642 B2 | 11/2004 | Ochi | |
| 2002/0056516 A1 | 5/2002 | Ochi | |
| 2005/0109442 A1 | 5/2005 | Neubauer et al. | |
| 2006/0021695 A1 | 2/2006 | Blessing et al. | |
| 2006/0024433 A1 | 2/2006 | Blessing et al. | |
| 2006/0048880 A1 | 3/2006 | Blessing et al. | |

FOREIGN PATENT DOCUMENTS

| | | |
|---|---|---|
| DE | 3413925 A1 | 10/1985 |
| DE | 43 35 919 A1 | 4/1995 |
| EP | 0 292 624 A1 | 11/1988 |
| EP | 0 958 801 A1 | 11/1999 |
| EP | 1 082 081 | 5/2002 |
| EP | 0 958 801 B1 | 9/2004 |
| EP | 1 621 167 A1 | 2/2006 |
| FR | 2 690 843 A1 | 11/1993 |
| JP | 60-232155 A | 11/1985 |
| JP | 63-59463 A | 3/1988 |
| JP | 4-200544 A | 7/1992 |
| JP | 7-150456 A | 6/1995 |
| JP | 11-318977 A | 11/1999 |
| JP | 11-320742 A | 11/1999 |
| JP | 2002-516191 A | 6/2002 |
| JP | 2006-16727 A | 1/2006 |
| RU | 2242291 C2 | 11/2003 |
| WO | WO 99/60964 A1 | 12/1999 |
| WO | WO 2005/072671 A1 | 8/2005 |

OTHER PUBLICATIONS

U.S. Appl. No. 12/373,786, Edvardsson et al., "An Apparatus and Method for Forming Air-Laid Absorbent Cores", filed Jan. 14, 2009.

U.S. Appl. No. 12/373,728, Edvardsson et al., "Mat-Forming Wheel", filed Jan. 14, 2009.

English language translation of the Russian Decision of Grant, dated Sep. 27, 2010, issued in corresponding Russian Patent Application, Application No. 2009105894.

Form PCT/ISA/210 (International Search Report) dated Mar. 6, 2007.

Form PCT/ISA/237 (Written Opinion of the International Searching Authority) dated Mar. 6, 2007.

Form PCT/IPEA/409 (International Preliminary Report on Patentability) dated Oct. 15, 2008.

Official Action issued on Aug. 16, 2011 by the Japanese Patent Office in corresponding Japanese Patent Application No. 2009-520699, and English language translation of the Official Action.

* cited by examiner

APPARATUS AND METHOD FOR FORMING AIR-LAID ABSORBENT CORES

TECHNICAL FIELD

The present disclosure relates to an apparatus for forming air-laid absorbent cores, comprising a first and second mat-forming wheel, each of the mat-forming wheels having a series of moulds along its peripheral surface, air-laying means for supplying air-entrained fibrous material to the moulds on each mat-forming wheel, suction means maintaining the formed core elements in the respective moulds during a part of the path of the moulds on the respective mat-forming wheel and means for transferring a core element on the second mat-forming wheel onto a core element on the first mat-forming wheel while the latter core element still is maintained in its mould, at least the air-laying means associated with the second mat-forming wheel comprises means for supplying a mixture of air-entrained fibrous material and discrete particles, and a method using such an apparatus.

BACKGROUND

Apparatuses of the kind referred to above are used to produce multi-layered absorbent cores, at least one of the layers containing discrete particles of a highly absorbent material, preferably a so called superabsorbent material (SAP), which can absorb liquid in an amount several times it own weight. The fibres in the layers are preferably cellulosic and produced by defibration of pulp. Additionally, other types of fibres can be added. The fibres in the different layers can be the same or different.

Apparatuses according to the present disclosure are to be disposed in a manufacturing line for producing absorbent articles, such as disposable diapers, sanitary napkins, incontinence protectors and the like sanitary articles. It is therefore important that such apparatuses do not occupy a lot of space, especially in the length direction of such a production line.

Nowadays, the production rate of such a production rate is high, approximately 600 cores per minute, and the present disclosure aims to allow even higher production rates. In such high speeds the centrifugal forces acting on the discrete particles in formed core elements are quite high and there is a problem of preventing these particles from falling out of such core elements. Apart from the cost consequence of losing relative expensive particle material, there is a risk that the lost particles will fall on components or equipment in the production line an adversely influence the functions thereof. Lost particles must therefore somehow be taken care of. There is therefore a need to keep such losses of particles as low as possible.

Another problem is to ensure that the core elements formed on the respective mat-forming wheel of an apparatus of the kind described in the introduction are superposed on each other in the desired mutual relationship. If, for example, the leading edges of the superposed core elements are to be aligned with each other, a misalignment will visually be very apparent and will also adversely influence the function of the produced article. For example, if the produced article contains openings or the like in the superposed cores which should coincide or have a determined relationship relative each other in the superposed position of the core elements, a misalignment of those openings will have a detrimental effect on the functioning of the produced article.

A further problem with an apparatus according to the introduction is that there is a risk that the discrete particles air-laid onto a mould will damage the mould or obstruct or clog some of the openings in the mould. Such obstructions or clogging leads to an uneven distribution of air-laid material in the mould and will consequently adversely affect the absorptive properties of the produced article.

In EP-B1-O 958 801 is shown an apparatus, in which a web of tissue is wound on a mat-forming wheel and drawn against the walls of the moulds on the peripheral surface of the wheel. Thereafter, a layer of discrete particles is air-laid in the mould and air-entrained fibres are drawn into this layer of discrete particles to mix with the discrete particles. In FIG. 3 of this document, such an apparatus having two mat-forming wheels is disclosed. The air-laid bodies are delivered from each mat-forming wheel attached to the webs of tissue and the two webs of tissue together with the attached bodies are then superposed on each other. The bodies attached to the webs travel a rather long distance without suction means influencing the bodies thereon and there is a great risk that particles will fall out of the bodies during this travel. Moreover, with such a construction it seems hard to obtain a great accuracy of the relative positions of the bodies attached to the webs when superposed to each other.

In EP-B1-1 082 081 an apparatus according to the preamble of Claim 1 is disclosed. In such an apparatus, only fibrous material is air-laid in the moulds on the first mat-forming wheel for forming a body on which a second body composed of a mixture of fibrous material and discrete particles of SAP is transferred from the second mat-forming wheel while the first body is still in its mould. A third layer of fibrous material is then air-laid over the composite of the first two bodies. During the transfer of the second body onto the first body, a part of the second body is always in the free air exposing both its sides thereto. There is thus a great risk that SAP-particles will fall out of these exposed parts of the second body, especially if the concentration thereof is high and the speed of the mat-forming wheels are high. After transfer of the second body onto the first body, the third layer air-laid thereon will prevent the SAP-particles in the second body from falling out. Although the accuracy of the positions of the superposed bodies is improved due to the first body being maintained in its mould during the transfer of the second body thereon, the second body has to move in free air before being superposed onto the first body, a fact that reduces accuracy. Moreover, in the second mat-forming wheel there are no means for preventing discrete particles air-laid in the moulds to obstruct or clog the openings in the bottoms of these moulds.

OBJECTS AND SUMMARY

It is an objective of the present disclosure to in an apparatus according to the introduction improve the accuracy of the transfer of a core element onto another, prevent air-laid discrete particles from damaging and/or clogging the moulds and prevent excessive losses of discrete particles from formed core elements. It is also an objective of the present disclosure to accomplish this without significantly increase the space required for the apparatus in a production line for the manufacturing of sanitary absorbent articles.

These objectives are accomplished by an apparatus for forming air-laid absorbent cores, comprising a first and second mat-forming wheel, each of the mat-forming wheels having at least one mould along its peripheral surface, air-laying means for supplying air-entrained fibrous material to the moulds on each mat-forming wheel, suction means maintaining the formed core elements in the respective moulds during a part of the path of the moulds on the respective mat-forming wheel and means for transferring a core element on the second mat-forming wheel onto a core element on the first mat-forming wheel while the latter core element still is maintained in its mould, at least the air-laying means associated with the second mat-forming wheel comprises means for supplying a mixture of air-entrained fibrous material and discrete particles, characterized by means for applying a protective layer to the bottom of each mould of at least the second mat-forming wheel, which protective layer has the function of protecting the mould from discrete particles during air-laying of a mixture of air-entrained fibrous material and discrete particles and for preventing discrete particles from exit out of the second core element during and after transfer, the two mat-forming wheels forming such a nip between each other that the second core element will abut the first core element before transfer. In such an apparatus the transfer of the second core element onto the first core element will be accomplished without any part of the second core element being in free air, i.e. when leaving the mould of the second mat-forming wheel the second core element will already be in abutment with the first core element and drawn thereto by suction means in the first mat-forming wheel. Furthermore, the protective layer applied to the bottom of the moulds of the second mat-forming wheel will be located on the outside of the second core element, i.e. the side being distal from the first core element, and will prevent discrete particles from leaving the second core element during and after transfer.

In a preferred embodiment the nip between the first and second mat-forming wheels is 10 mm at the most and both the first and second mat-forming wheel include means for supplying a mixture of air-entrained fibrous material and discrete particles and means for applying a protective layer to the bottom of each mould of the first and second mat-forming wheel. Moreover, means for applying a first web of casing material onto the composite core leaving the nip between the first and second mat-forming wheels, are positioned so that said web is applied to the composite core before this core is delivered from the first mat-forming wheel. Means are preferably arranged for applying a second web of casing material onto the composite core, composed of the two core elements and the first web, immediately after this composite core has been brought to leave the first mat-forming wheel and to fasten the webs to each other.

In a first preferred embodiment, said means for applying a protective layer to the bottom of each mould of a mat-forming wheel are air-lying means for supplying air-entrained fibrous material to the moulds on the mat-forming wheel.

In a second preferred embodiment, said means for applying a protective layer to the bottom of each mould of a mat-forming wheel are means for applying a web of air-permeable casing material to the mat-forming wheel, whereby said suction means associated with the moulds will draw the material in the web to abutment against the walls of each mould. Means for applying an adhesive coating on the side of said webs distal from the bottom of the moulds are suitably arranged.

In a third preferred embodiment, said means for applying a protective layer to the bottom of each mould of the second mat-forming wheel are air-lying means for supplying air-entrained fibrous material to the moulds on the second mat-forming wheel and said means for applying a protective layer to the bottom of each mould of the first mat-forming wheel are means for applying a web of air-permeable casing material to the mat-forming wheel, whereby said suction means associated with the moulds will draw the material in the web to abutment against the walls of each mould In all embodiments the moulds on the second mat-forming wheel has preferably a smaller extension at least in a peripheral direction than the moulds on the first mat-forming wheel and the moulds in the series of moulds on the first and second mat-forming wheel are preferably so arranged that a core element formed in the moulds of the second mat-forming wheel is transferred to a core element formed in the moulds of the first mat-forming wheel with its leading edge aligned with the leading edge of the core element in the mould on the first mat-forming wheel.

The disclosure also relates to a method of forming air-laid absorbent cores, comprising the steps of: forming first and second core elements by air-laying of air-entrained fibrous material to moulds on a first and second mat-forming wheel, each of said mat-forming wheels having a series of moulds along their peripheral surface, whereby at least the air-laying means associated with the second mat-forming wheel comprises means for supplying a mixture of air-entrained fibrous material and discrete particles; transferring a core element on the second mat-forming wheel onto a core element on the first mat-forming wheel while the latter core element still is maintained in its mould by suction means, characterized by applying a protective layer to the bottom of each mould of at least the second mat-forming wheel before air-laying of a mixture of air-entrained fibrous material and discrete particles in the mould, which protective layer has the function of protecting the mould from discrete particles during air-laying of a mixture of air-entrained fibrous material and discrete particles and for preventing discrete particles from exit out of the second core element during and after transfer, and forming such a nip between the two mat-forming wheels that the second core element will abut the first core element before transfer.

In a preferred embodiment the nip formed between the first and second mat-forming wheels is 10 mm at the most. Preferably, a mixture of air-entrained fibrous material and discrete particles is supplied to both the first and second mat-forming wheel and a protective layer is applied to the bottom of each mould on the first and second mat-forming wheel. A first web of casing material is suitably applied onto the composite core leaving the nip between the first and second mat-forming wheels, and said first web is positioned so that said web is applied to the composite core before this core is delivered from the first mat-forming wheel and a second web of casing material is applied onto the composite core, composed of the two core elements and the first web, immediately after this composite core has been brought to leave the first mat-forming wheel and the webs are fastened to each other.

In a first variant of the method, a fibrous protective layer is air-laid on the bottom of each mould of a mat-forming wheel.

In a second variant, a web of air-permeable casing material is applied to the mat-forming wheel to form said protective layer to the bottom of each mould of a mat-forming wheel, whereby said suction means associated with the moulds will draw the material in the web to abutment against the walls of each mould, and an adhesive coating is applied on the side of said webs distal from the bottom of the moulds.

In a third variant, a fibrous protective layer is air-laid to the bottom of each mould of the second mat-forming wheel and a web of air-permeable casing material is applied to the first mat-forming wheel, whereby said suction means associated with the moulds will draw the material in the web to abutment against the walls of each mould The moulds on the second mat-forming wheel is preferably given a smaller extension, at least in a peripheral direction, than the moulds on the first mat-forming wheel. The moulds in the series of moulds on the first and second mat-forming wheel are preferably so arranged that a core element formed in the moulds of the second mat-forming wheel is transferred to a core element formed in the moulds of the first mat-forming wheel with its leading edge aligned with the leading edge of the core element in the mould on the first mat-forming wheel.

BRIEF DESCRIPTION OF THE DRAWINGS

The disclosure will now be described with reference to the enclosed Figures, which are for the purpose of illustration of various non-limiting embodiments of the disclosure, of which.

DESCRIPTION OF EMBODIMENTS

Figure 1:
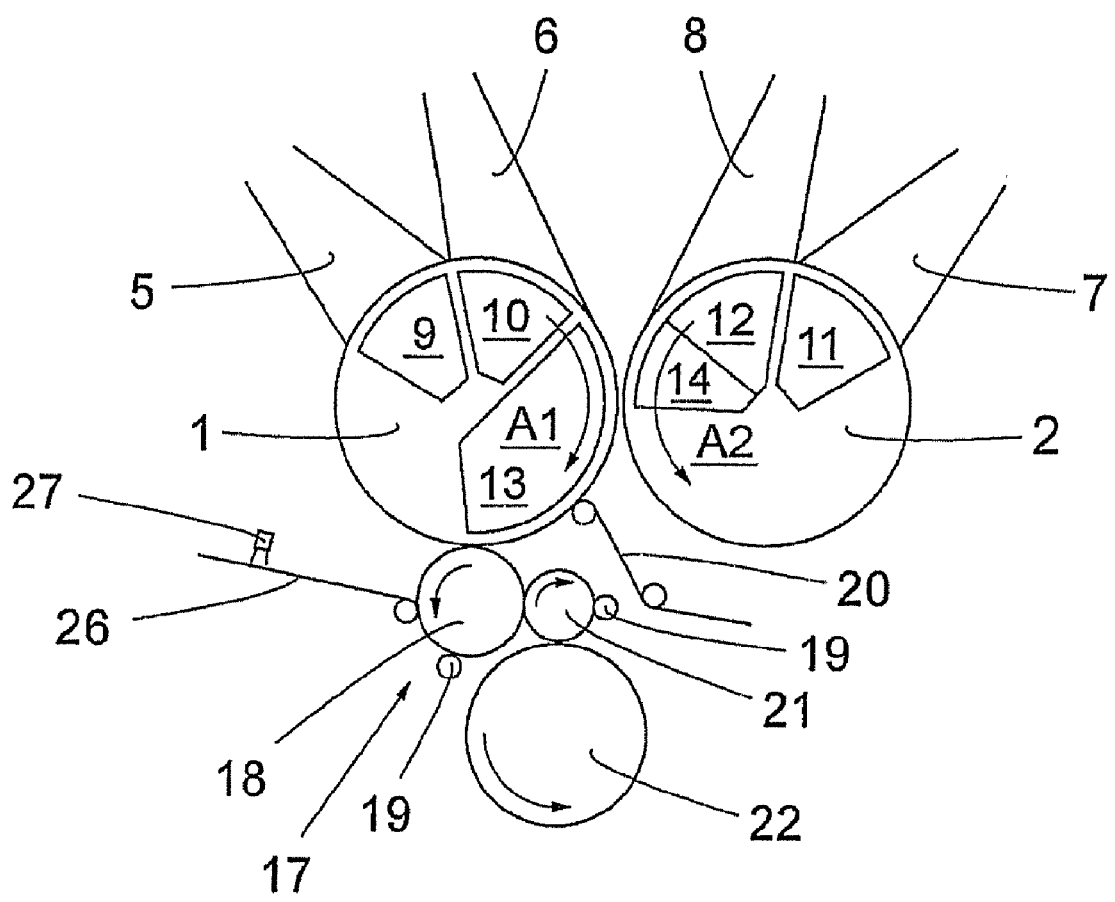
FIG. 1 schematically shows a side view of an apparatus for forming air-laid absorbent cores according to a first preferred embodiment of the disclosure, FIG. 2 schematically shows a sectional side view of a part of the apparatus in FIG. 1 in a larger scale, and FIG. 3 schematically discloses a side view of an apparatus for forming air-laid absorbent cores according to a second preferred embodiment.
Figure 2:
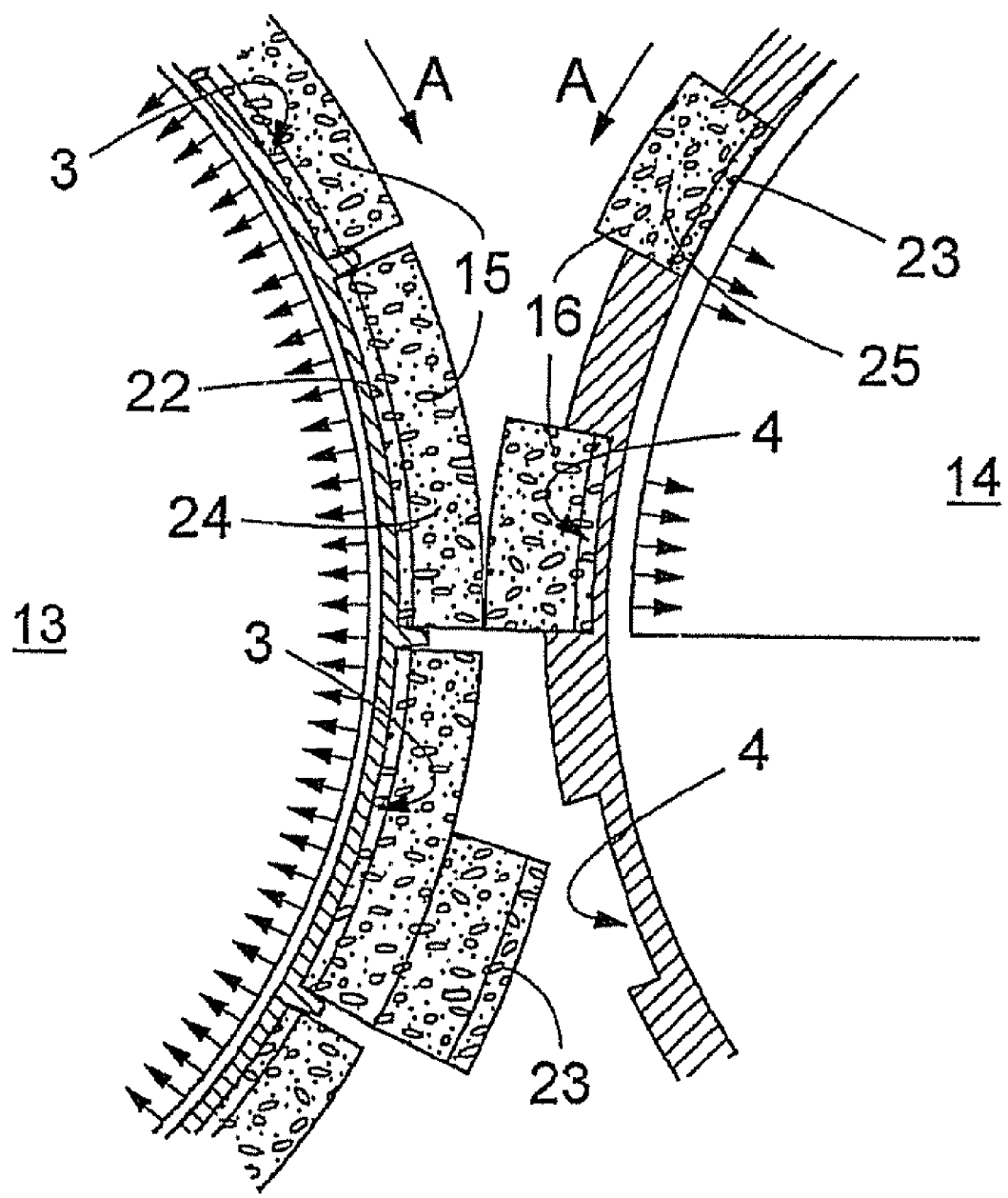

In FIGS. 1 and 2, a first preferred embodiment of an apparatus for forming air-laid absorbent cores is schematically disclosed. The apparatus includes two formation drums or mat-forming wheels, a first wheel 1 and a second wheel 2, each having a series of moulds 3 and 4 (see FIG. 2), respectively, on their peripheral surfaces. The mould bottom or screen can be made of wire mesh or perforated steel sheet. Associated to the peripheral surfaces of the two mat-forming wheels 1,2 are two formation chambers or hoods 5,6 and 7,8, respectively, for each wheel. The apparatus also comprises a mill, for example a hammer mill, for defibrating of pulp, pipes used for fibre or fibre/SAP transport, and a fan for the transport of fibre or fibre/SAP to the respective hood 5-8. These components are conventional and well know to one skilled in the art and will not be further described. For the understanding of the present disclosure it is enough to say that a homogenous mixture of air fibres and eventually SAP-particles are present in the hoods 5-8 when the apparatus is in use. Each hood 5-8 is associated with a separate suction box 9,10 and 11,12, respectively, which is stationary and located in the interior of the respective mat-forming wheel, i.e suction boxes 9,10 are disposed inside the first wheel 1 and suction boxes 11,12 are disposed inside the second wheel 2. When the moulds on the peripheral surface of each wheel pass between a hood and its associated suction box during the rotation of the wheel, the air-entrained material in the hood will be drawn into the mould and deposited therein. In the mat-forming wheels 1,2, suction boxes 13 and 14, respectively, are present for maintaining the core elements formed in the moulds in the their respective mould and for maintaining the shape of the formed core elements.

The mat-forming wheels 1,2 are disposed side-by-side, the nip between them being dimensioned to be at least 6 mm. The term "nip" denotes the point at which the peripheries of the wheels 1,2 are closest to each other.

In the apparatus according to FIGS. 1 and 2, the second core element 16 (see FIG. 2) formed on the second mat-forming wheel 2 is transferred onto the first core element 15 formed on the first mat-forming wheel 1 and held thereon by the suction created by suction box 13 until the composite core comprising core elements 15,16 is delivered to a compression device 17 consisting of two rollers 18,19. Near the nip between the wheels 1 and 2 and between the nip and the compression device 17, a web 20 of casing material, for example tissue, from a supply roll (not shown) is applied to the outer side of the composite core 15,16.

After compression, the composite core passes through a cutting device 21 and is then transferred to an accelerator device 22 before it is delivered into the line for manufacturing of absorbent articles of which the apparatus according to the disclosure is a part.

A method of using the apparatus illustrated in FIGS. 1 and 2 will now be described.

As the mat-forming wheels 1,2 rotates in the direction of arrows A1 and A2, the moulds 3 and 4, respectively, first passes between the hood 5 respective 7 and the suction box 9 respective 11. During this passage a thin layer of about 1 mm of pure pulp fibres 22 respective 23 (see FIG. 2) is air-laid in the moulds 3,4. Thereafter the moulds 3,4 on the respective mat-forming wheel pass between the hood 6 respective 8 and suction box 10 respective 12. During this passage a layer 24 respective 25 of a mixture of pulp fibres and SAP-particles is air-laid in the moulds 3 and 4 covering the layer of pure pulp fibres. The layer 24 has a thickness of 5 mm and the layer 25 has a thickness of 5 mm. The concentration of SAP-particles in layer 24 is much lower than in layer 25. Layer 24 can have a concentration of SAP-particles of about 10-30 wt % and layer 25 about 50-70 wt %. The layers 22,23 of pure pulp fibres have the functions of preventing SAP-particles from obstructing and clogging the holes in the mould bottom, thereby causing an uneven distribution of air resulting in an uneven distribution of air-laid material, and from damaging the mould bottom. It has surprisingly been shown that SAP-particles in a mixture of pulp fibres and SAP-particles can wear out the material in the mould bottoms. The layers 22,23 also have the function of preventing SAP-particles from falling out of the core element formed in the respective mould during transport of the moulds on the respective wheel, during transfer of the second core element 16 onto the first core element 15 and during transfer of the composite core from wheel 1 to the compression device.

As is evident from FIG. 2, the moulds 3 and 4 are shallower than the core elements 15 respective 16 formed therein. After the core elements 15,16 have been formed by air-laying of layers 22,24 and 23,25, respectively in the respective moulds 3,4, the core elements 15,16 are maintained in their respective mould by suction boxes 13 respective 14 until they reach the nip between the mat-forming wheels 1,2.

According to the present disclosure, the nip is dimensioned so that the outsides of the core elements 15,16, i.e. the sides thereof distal from the respective mould bottom, abut each other in the nip. In other words, the nip constitutes a "marrying point" for the two core elements 15,16 in which they get together. The nip is preferably dimensioned so that normally the core elements 15,16 are slightly compressed in the marrying point. The suction box 14 in the second mat-forming wheel 2 ends at the marrying point. When the leading edge of the core element 16 during the continued rotation of wheels 1,2 leaves the marrying point it will no longer be subjected to suction forces maintaining it on wheel 2 but only the suction forces of suction box 13 on wheel 1. These suction forces will maintain the leading edge of core element 16 in abutment with the leading edge of core element 15 in a mould 2 of wheel 1. Due to the arrangement of the nip and the "overfilling" of moulds 3 and 4, respectively, all points of a core element 16 will in the nip come to abutment with the outside of core element 15 while core element 16 still is maintained in mould 4 and is not until then transferred onto a core element 15. Thus an extremely controlled and accurate transfer of core elements 15,16 is accomplished. The core element 16 is thus subjected to suction forces from either suction box 14 on wheel 2 or suction box 13 during the whole transfer. No part of the core element 16 is thus left in free air during transfer. Losses of SAP-particles out of core element 16 is thereby significantly reduced in relation to a transfer operation in which the core element or portions thereof are moving in free air when centrifugal and gravitation forces are not counteracted by suction forces.

After the core element 16 has been transferred to wheel 1 onto the core element 15, the thin protective layer 23 of core element 16 will prevent SAP-particles from falling out of this core element.

However, core element 15 has a longer extension at least in circumferential direction of wheel 1 and has no protection against loss of SAP-particles in its trailing end part. Although the suction forces of suction box 13 counteract the centrifugal and gravitational forces is it advisable to protect this trailing end part as soon as possible. This is accomplished by the web 20 of casing material, e.g. tissue, applied to the composite core 15,16 transported on the wheel 1 after passing of the nip. Another reason for applying such a web is that the compressing step in the compressing device 17 will be facilitated if the core is encapsulated in tissue from both sides during the compression. In order to accomplish this a further web 26 of casing material is applied to the side of core 15,16 opposite to the side to which web 20 is applied after the core 15,16 have left wheel 1 but before it passes between the rollers 18,19 of the compression device. Preferably, an adhesive coating is applied to web 26 by a glue applicator 27 before it is applied to the composite core 15,16.

Figure 3:
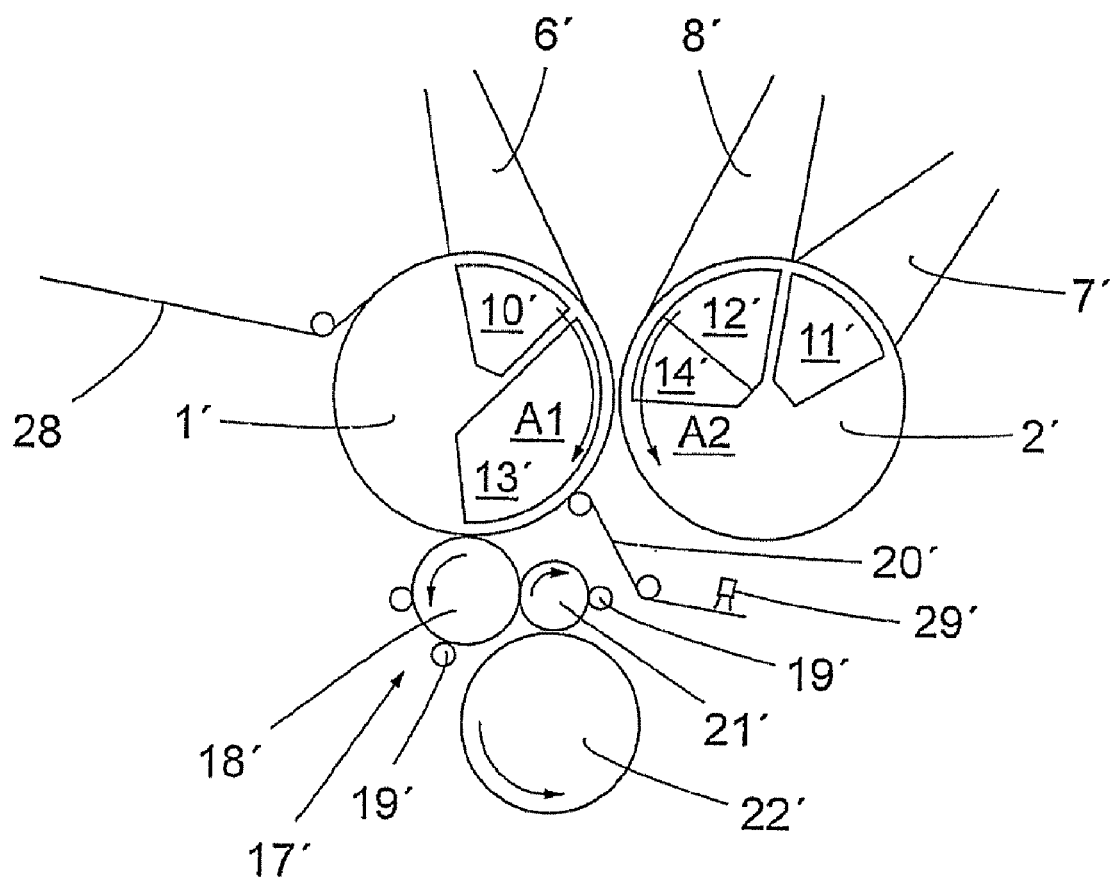

In FIG. 3, a second embodiment of an apparatus according to the present disclosure is illustrated. The apparatus in FIG. 3 differ from the apparatus in FIGS. 1 and 2 in principle only in respect of the construction of the protective layer to the bottoms of the moulds on the first mat-forming wheel and components in the apparatus according to FIG. 3 similar to components in the apparatus according to FIGS. 1 and 2 are given the same reference numerals with the addition of a prime sign.

In the second embodiment according to FIG. 3, the protective layer of pure pulp air-laid in the moulds 3 of the first mat-forming wheel 1 in the embodiment according FIGS. 1 and 2 has been substituted by a web 28 of nonwoven in the apparatus according to the second embodiment. The web of nonwoven 28 is applied to the peripheral surface of mat-forming wheel 1' upstream of the hood 6' seen in the rotational direction A1 of this wheel. As a consequence of the substitution of a layer of pure pulp with a web 28 of nonwoven, the hood and suction box for air-laying of such a layer is no longer present in the second embodiment of the apparatus. Moreover, the web of nonwoven also functions as a casing material which means that the web 26 of casing material in the apparatus according to the embodiment shown FIG. 1 is not present in the second embodiment of an apparatus according to the present disclosure. Before web 20' is applied to the mat-forming wheel 1' it is coated with an adhesive by a glue applicator 29'.

The nonwoven material can be a web of polypropene (PP), polyethylene (PE), preferably a nonwoven of fibres of PP with a basis weight lower than 20 g/m2, preferably lower than 15 g/m2 in order to have a web which has good air-permeability and a low penetrability for SAP.

When a mould 3' covered by the applied web 28 enters the area between the hood 6' and the suction box 10', the web 28 will be drawn against the bottom of the mould by the suction forces and form a protective layer therein function in the same way as the thin layer of pulp air-laid in the moulds according to the first embodiment of the apparatus.

Instead of a web of nonwoven material a web of tissue might be used. However, nonwoven material is preferred since a web of tissue might have to be to thick in order to have the necessary strength.

In all other respects an apparatus according to the second embodiment functions in the same way as described in relation to the apparatus according to the first embodiment and has the same advantageous properties of accurate transfer and small losses of SAP-particles. It is also advantageous in respect of number of components needed for producing absorbent bodies in accordance with the described method.

An apparatus according to the embodiments shown enables a production of absorbent cores at a very high rate of even more than 600 cores per minute.

The apparatuses according to the described embodiments can of course be modified in several respects without leaving the scope of disclosure. For example, the thin protective layer air-laid in the moulds of the second mat-forming wheels can be substituted by a nonwoven web in the same way as in the second embodiment either instead of substituting the thin protective layer in the moulds of the first mat-forming wheel or as a complement thereto. The dimensions of the core elements can be different than shown and the leading edges of the two superposed core elements need not be aligned but the second core element can be disposed anywhere in relation to the first core element. The compression device, cutting device and accelerator for delivering produced cores to the production line for the manufacturing of absorbent articles can be any type of such equipment used in such production line. The disclosure shall therefore only be limited of the wording of the granted patent claims.

The invention claimed is:

1. An apparatus for forming air-laid absorbent cores, the apparatus comprising:
   first and second mat-forming wheels, each of the mat-forming wheels having at least one mould along its peripheral surface,
   air-laying means for supplying air-entrained fibrous material to the at least one mould on each mat-forming wheel,
   suction means for maintaining the formed core elements in the respective moulds during a part of the path of the moulds on the respective mat-forming wheel, and
   means for transferring a core element on the second mat-forming wheel onto a core element on the first mat-forming wheel while the core element on the first mat-forming wheel is maintained in its mould, each mould on the first mat-forming wheel having a depth which is smaller than a thickness of the core element on the first mat-forming wheel in a radial direction of the first mat-forming wheel,
   wherein at least the air-laying means associated with the second mat-forming wheel comprises means for supplying a mixture of air-entrained fibrous material and discrete particles,
   the apparatus further comprising:
   means for applying a protective layer to the bottom of each mould of at least the second mat-forming wheel, which protective layer has the function of protecting the mould from discrete particles during air-laying of a mixture of air-entrained fibrous material and discrete particles and for preventing discrete particles from exiting out of the second core element during and after transfer onto the core element of the first mat-forming wheel, the two mat-forming wheels forming a nip between each other such that the second core element will abut the first core element in the nip before transfer.

2. The apparatus according to claim 1, wherein the nip between the first and second mat-forming wheels is 10 mm at the most.

3. The apparatus according to claim 2, wherein both the first and second mat-forming wheels include means for supplying a mixture of air-entrained fibrous material and discrete particles and means for applying a protective layer to the bottom of each mould of the first and second mat-forming wheels.

4. The apparatus according to claim 2, further comprising means for applying a first web of casing material onto the composite core leaving the nip between the first and second mat-forming wheels,
  wherein the means are positioned so that said web is applied to the composite core before the composite core is delivered from the first mat-forming wheel.

5. The apparatus according to claim 4, further comprising means for applying a second web of casing material onto the composite core, the composite core comprising the two core elements and the first web,
  wherein the means for applying the second web are arranged to apply the second web immediately after this composite core has been brought to leave the first mat-forming wheel and to fasten the webs to each other.

6. The apparatus according to claim 1, wherein said means for applying a protective layer to the bottom of each mould of a mat-forming wheel are air-lying means for supplying air-entrained fibrous material to each mould on the mat-forming wheel.

7. The apparatus according to claim 1, wherein said means for applying a protective layer to the bottom of each mould of a mat-forming wheel are means for applying a web of air-permeable casing material to the mat-forming wheel whereby said suction means associated with each mould will draw the material in the web to abutment against the walls of each mould.

8. The apparatus according to claim 1, wherein said means for applying a protective layer to the bottom of each mould of the second mat-forming wheel are air-lying means for supplying air-entrained fibrous material to each mould on the second mat-forming wheel and said means for applying a protective layer to the bottom of each mould of the first mat-forming wheel are means for applying a web of air-permeable casing material to the mat-forming wheel, whereby said suction means associated with each mould will draw the material in the web to abutment against the bottom of each mould.

9. The apparatus according to claim 1, wherein a web of casing material is applied to each of the first and second mat-forming wheels and means are arranged for apply an adhesive coating on the side of said webs distal from the bottom of the moulds.

10. The apparatus according to claim 1, wherein each mould on the second mat-forming wheel has a smaller extension at least in a peripheral direction than each mould on the first mat-forming wheel.

11. The apparatus according to any claim 1, wherein each of the first and second mat-forming wheels comprises a series of moulds, wherein the moulds in the series of moulds on the first and second mat-forming wheels are so arranged that a core element formed in the moulds of the second mat-forming wheel is transferred to a core element formed in the moulds of the first mat-forming wheel with its leading edge aligned with the leading edge of the core element in the mould on the first mat-forming wheel.

12. A method of forming air-laid absorbent cores, the method comprising the steps of:
  forming first and second core elements by air-laying of air-entrained fibrous material to moulds on first and second mat-forming wheels, each of said mat-forming wheels having at least one mould along its peripheral surface, whereby at least the air-laying means associated with the second mat-forming wheel comprises means for supplying a mixture of air-entrained fibrous material and discrete particles;
  transferring a core element on the second mat-forming wheel onto a core element on the first mat-forming wheel while the core element on the first mat-forming wheel is maintained in its mould by suction means,
  the method further comprising:
  applying a protective layer to the bottom of each mould of at least the second mat-forming wheel before air-laying of a mixture of air-entrained fibrous material and discrete particles in the mould, which protective layer has the function of protecting the mould from discrete particles during air-laying of a mixture of air-entrained fibrous material and discrete particles and for preventing discrete particles from exiting out of the second core element during and after transfer, and
  forming a nip between the two mat-forming wheels such that the second core element will abut the first core element in the nip before transfer.

13. The method according to claim 12, wherein the nip formed between the first and second mat-forming wheels is at least 6 mm.

14. The method according to claim 13, wherein a mixture of air-entrained fibrous material and discrete particles is supplied to both the first and second mat-forming wheels and a protective layer is applied to the bottom of each mould on the first and second mat-forming wheels.

15. The method according to claim 13, further comprising applying a first web of casing material onto the composite core leaving the nip between the first and second mat-forming wheels,
  wherein said first web is positioned so that said web is applied to the composite core before the composite core is delivered from the first mat-forming wheel.

16. The method according to claim 15, further comprising applying a second web of casing material onto the composite core, the core composed of the two core elements and the first web, immediately after this composite core has been brought to leave the first mat-forming wheel and the webs are fastened to each other.

17. The method according to claim 12, further comprising air-laying a fibrous protective layer on the bottom of each mould of a mat-forming wheel.

18. The method according to claim 12, further comprising applying a web of air-permeable casing material to the mat-forming wheel to form said protective layer to the bottom of each mould of a mat-forming wheel, whereby said suction means associated with each mould will draw the material in the web to abutment against the walls of each mould.

19. The method according to claim 12, further comprising air-laying a fibrous protective layer to the bottom of each mould of the second mat-forming wheel and
  applying a web of air-permeable casing material to the first mat-forming wheel,
  whereby said suction means associated with each mould will draw the material in the web to abutment against the walls of each mould.

20. The method according claim 12, further comprising applying a web of casing material to each of the first and second mat-forming wheels and applying an adhesive coating on the side of said webs distal from the bottom of the moulds.

21. The method according to claim 12, wherein each mould on the second mat-forming wheel has a smaller extension at least in a peripheral direction than each mould on the first mat-forming wheel.

22. The method according to claim 12, wherein each of the first and second mat-forming wheels comprises a series of moulds, wherein the moulds in the series of moulds on the first and second mat-forming wheels are so arranged that a core element formed in the moulds of the second mat-forming wheel is transferred to a core element formed in the moulds of the first mat-forming wheel with its leading edge aligned with the leading edge of the core element in the mould on the first mat-forming wheel.

\* \* \* \* \*